United States Patent
Dreux et al.

(10) Patent No.: US 6,936,174 B2
(45) Date of Patent: Aug. 30, 2005

(54) METHOD FOR CONTROLLING AN EVAPORATIVE LIGHT SCATTERING DETECTOR WHICH IS COUPLED TO A LIQUID CHROMATOGRAPHY COLUMN

(75) Inventors: Michel Dreux, Olivet (FR); Henry Gangloff, Charentou le Pont (FR)

(73) Assignee: Sedere, Alfortville Cedex (FR)

( * ) Notice: Subject to any disclaimer, the term of this patent is extended or adjusted under 35 U.S.C. 154(b) by 0 days.

(21) Appl. No.: 10/774,074

(22) Filed: Feb. 6, 2004

(65) Prior Publication Data

US 2004/0200777 A1 Oct. 14, 2004

(30) Foreign Application Priority Data

Feb. 12, 2003 (FR) ............................................. 03 01652

(51) Int. Cl.⁷ ............................................... B01D 15/08
(52) U.S. Cl. .................... 210/659; 210/656; 210/198.2; 73/61.58; 250/574; 436/161
(58) Field of Search ................................ 210/635, 656, 210/659, 198.2; 73/61.52, 61.58; 436/161; 250/574

(56) References Cited

U.S. PATENT DOCUMENTS 6,077,438 A 6/2000 Zambias et al.
6,151,113 A * 11/2000 O'Donohue et al. ........ 356/338
6,402,946 B1 6/2002 Spraul et al.
2001/0038071 A1 11/2001 Nichols et al.
2002/0072126 A1 * 6/2002 Chervet et al. ............. 436/161

FOREIGN PATENT DOCUMENTS

EP 1275961 A 1/2003

* cited by examiner

Primary Examiner—Ernest G. Therkorn
(74) Attorney, Agent, or Firm—Baker & Daniels

(57) ABSTRACT

Method allowing control of an evaporative light scattering detector which is coupled to a liquid chromatography column, substantially independently of the elution conditions for the chromatographic separation.

A given adjustable constant calibrated volume of the flow which originates from the chromatography column is removed at a given adjustable frequency, this flow being constituted by an eluent which contains compounds to be analysed which have been dissolved therein, and the volume removed in this manner is transferred to a secondary circuit, to which the evaporative light scattering detector is connected, by being conveyed by means of an auxiliary pump with a specific carrier fluid which is independent of the eluent having a predetermined flow, and the successive fractions of the flow which originates from the chromatography column are mixed with the carrier fluid which conveys these fractions upstream of the evaporative light scattering detector.

7 Claims, No Drawings

METHOD FOR CONTROLLING AN EVAPORATIVE LIGHT SCATTERING DETECTOR WHICH IS COUPLED TO A LIQUID CHROMATOGRAPHY COLUMN

The present invention relates to a method which allows control of an evaporative light scattering detector which is coupled to a liquid chromatography column, substantially independently of the elution conditions for the chromatographic separation.

Liquid chromatography is widely used by analysts in order to separate different constituents of a mixture with a view to identifying and/or analysing them.

The principle thereof is based on the different types of interaction of these constituents with a stationary phase filling the chromatography column.

In order to carry out a separation by chromatography in the liquid phase, the mixture for analysis is introduced at the input of the column, then a mobile phase, known as the eluent, which is constituted by a given flow of a solvent or a series of solvents, which are selected in increasing order of affinity for the stationary phase (separation by elution gradient), is introduced therein.

Consequently, a chronological flow which is constituted by an eluent, in which the constituents of the mixture to be analysed which have previously been separated are successively dissolved, is collected at the output of the column.

In order to identify and/or analyse the compounds separated in this manner, it is necessary to couple a detector, which is located downstream of the chromatography column, to the liquid chromatography column.

Liquid chromatography still suffers today from the absence of a universal detector which is convenient to use and very sensitive.

In order to analyse the flows originating from the liquid chromatography columns, analysts conventionally use, as a detector of the universal type, either differential refractometers or evaporative light scattering detectors.

However, refractometers are not sensitive and have been found to be of limited use in chromatography in the isocratic mode, which means that they are currently used only when analysts have no other choice.

Evaporative light scattering detectors are more sensitive than refractometers and are compatible with chromatography in the gradient mode. They have the advantage of allowing the analysis of all of the non-volatile compounds, in particular the inorganic or organic cations and anions which are present in a sample, without any preparation of the sample or special prior chemical processing.

However, such a detector has the disadvantage of allowing the detection only of analytes which are less volatile than the liquid phase (eluent) which carries them.

In the case of analytes having intermediate volatility (semi-volatile analytes), it is further necessary to carry out the detection at a low vaporising temperature of the liquid phase, which involves more limited analysis conditions and reduced sensitivity.

Another criticism levelled at the evaporative light scattering detector is linked to the polluting features thereof, given that it requires the volatilisation of the eluent, that is to say, in particular of organic solvents.

The operating principle of an evaporative light scattering detector is as follows: the compounds to be analysed are transported by a mobile phase or a more volatile carrier liquid which is then nebulised and evaporated at a relatively low temperature (being able to be in the order of from 30 to 40° C.) so that residual micro-particles alone remain—ideally the compounds to be analysed—which can be detected by light scattering.

In this manner, it is possible to analyse directly effluents which originate from chromatography columns under the condition of selecting a mobile phase which is volatile enough to be directly used as a carrier liquid for the evaporative light scattering detector.

Evaporative light scattering detectors comprise:

a nebuliser which is associated with a nebulisation chamber and in which, on the one hand, a sample which is constituted by a carrier liquid, which contains less volatile compounds to be analysed which have been dissolved therein, is introduced and, on the other hand, a nebulising gas which allows the sample to be converted into an aerosol, a drift tube which is constituted by a heated tube, in which the carrier liquid is evaporated in order to conserve only micro-particles of the compounds to be analysed, and a detection chamber, in which the residual micro-particles of the compounds to be analysed are irradiated with radiation which originates from a polychromatic or monochromatic source, and the light scattered in a different direction from that of the irradiation beam is detected.

When the evaporative light scattering detector is coupled to a chromatography column which is located upstream thereof, a chromatogram which is constituted by a chronological succession of signals (peaks), which ideally each represent a compound of the mixture to be analysed, is obtained in this manner; the area of these signals (peaks) is a function of the concentration or the mass of each compound in the starting sample.

If A represents the area of the signal which measures the intensity which is emitted by a mass m or a concentration c ($m=V\times c$, V being the volume introduced) of one of the compounds to be analysed, these two values are linked by the general formula: $A=am^b$ or, in other words, $\text{Log } A = b \text{ Log } m + \text{Log } a$.

The logarithm of the area of the signal which measures the intensity emitted by a compound to be analysed is therefore a linear function of the logarithm of the mass (or the concentration) of this compound in the sample.

In order to carry out a quantitative analysis, therefore, a calibration curve is plotted beforehand and the mass or the concentration of a compound to be analysed, corresponding to the intensity of the light scattered by this compound, is read off from the line.

The value of coefficient b corresponds to the slope of the calibration curve or the response coefficient of the detector relative to this specific compound.

The object of the present invention is to overcome the disadvantages of the conventional methods for analysing flows which originate from liquid chromatography columns by means of an evaporative light scattering detector and, to this end, proposes a method for controlling such a detector, allowing precise and reliable detection of a greater number of analytes, substantially independently of the elution conditions for the chromatographic separation, and further being capable of reducing to a large extent the pollution brought about thereby.

According to this method, a given adjustable constant calibrated volume (or a given adjustable constant calibrated mass) of the flow which originates from the chromatography column is removed at a given adjustable frequency, this flow being constituted by an eluent which contains compounds to be analysed which have been dissolved therein, and the volume removed in this manner is transferred to a secondary circuit, to which the evaporative light scattering detector is connected, being conveyed by means of an auxiliary pump with a specific carrier fluid which is independent of the eluent and which has a predetermined flow, and the successive fractions of the flow which originates from the chromatography column are mixed with the carrier fluid which conveys these fractions upstream of the evaporative light scattering detector.

Therefore, it is necessary for, on the one hand, a module for transferring effluents, which module is constituted by a particular active flow-division valve as well as an auxiliary pump which can convey the effluents transferred by means of a carrier fluid to the secondary circuit in order to allow it to convey the fractions of the flow which originates from the chromatography column, and, on the other hand, a device for mixing successive fractions with the carrier fluid, to be associated with the evaporative light scattering detector, downstream of the chromatography column, when the method according to the invention is used.

By way of example, an active flow-division valve of the same type as the valve described in document US2001/003807.1-A1 and marketed by Company RHEODYNE could be used to this end.

This valve, which was designed to allow the control of a collection of fractions during preparative chromatography by means of a mass spectrometer comprises internal fluid circuits which allow the selective connection of a calibration loop to a principal circuit or separation circuit or to a secondary circuit or detection circuit.

Therefore, the calibration loop is, in a first phase, filled with liquid which originates from the principal circuit, then, in a second phase, this volume of liquid is transferred to the secondary circuit.

However, so that such a valve can be used during quantitative analysis, in particular in the case of low flow rates, it is necessary to modify the internal fluid circuits thereof in order to ensure the transfer of a constant volume of liquid, whatever the characteristics, in particular the viscosity, of the liquid in the principal circuit.

Consequently, the method according to the invention is most particularly suitable for the separation of analytes by elution gradient: the proportion of the principal flow which originates from the chromatography column that is transferred to the secondary circuit is constant and independent of the nature, in particular the viscosity, of the eluent which is used on the chromatography column.

In this manner, it is therefore possible to attenuate the variations in the response of the evaporative light scattering detector which are conventionally observed and which are a function of the nature of the eluent.

Conversely, the conventional flow-division valves correspond to passive valves which are substantially constituted by a T-shaped tubing which comprises three branches, the diameters and the lengths of which are determined in accordance with the division ratio selected which depends on the flow and the viscosity of the mobile phase.

Consequently, using such flow-division valves necessitates modification of the assembly when the eluent is changed so that these valves are not well-suited to the division in a constant ratio of a flow which originates from a column for the separation of analytes by elution gradient.

Taking the above into consideration, the method according to the invention can be adapted to liquid chromatography, analytical chromatography, preparative chromatography or chromatography with a low flow rate, but also to counter-current chromatography and other types of separation carried out in the liquid phase.

Another particularly interesting advantage of the method according to the invention is linked to the polyvalent characteristics thereof; with a single assembly and for a given flow of eluent on the chromatography column, it is possible to obtain a plurality of different division ratios or a plurality of different mass transfers, by the calibrated volumes which are transferred to the secondary circuit and the transfer frequencies being varied.

Consequently, and according to another feature of the invention, in the presence of majority compounds and minority compounds, the calibrated volumes transferred to the secondary circuit and the transfer frequencies are varied during analysis.

In this manner, it is possible to facilitate the simultaneous determination of compounds having very weak concentrations in the presence of compounds at high concentrations by different adjustment of the ratios for mass transfer.

It should further be noted that the method according to the invention allows, by transferred masses being mixed and diluted, the saturation of the evaporative light scattering detector to be prevented by means of suitable adjustment of the flow of carrier fluid and/or the ratio for mass transfer.

In order to reconstitute the chromatographic peaks in the evaporative light scattering detector, however, it is necessary to select the transfer parameters so that the number of transfers corresponding to a given peak is sufficient to allow this peak to be reconstituted.

In the case of a quantitative analysis, it is necessary in practice to have at least eight transfers in order to be able to reconstitute a peak; consequently, for a given flow of eluent, it is necessary to take into consideration this requirement when the transfer frequency is selected.

On the other hand, if a qualitative analysis only is desired, the number of transfers can be smaller.

The possibility for the analyst of selecting the flow and the composition of the carrier fluid further offers the advantage of allowing a considerable reduction in the pollution inherent to the current operation of evaporative light scattering detectors; by way of example, in the case of a flow of the eluent of 1 ml per minute on the chromatography column and a division ratio of 20, a flow as low as 50 $\mu$l per minute in the secondary circuit can be used, which also reduces the pollution by a factor of 20.

Furthermore, it is still possible to select a carrier fluid which is less polluting than the eluent used on the chromatography column.

The significant advantage of the method according to the invention is, however, linked to its almost-total independence from the elution conditions for the chromatographic separation, which allows quantitative analyses to be carried out which were previously impossible, and further offers analysts the possibility of adjusting the response of the evaporative light scattering detector in accordance with the desired objectives.

In this regard, it should be noted that analysts constantly criticise the evaporative light scattering detector for not allowing sufficiently precise and reliable analyses, or for not having a linear response, which complicates the analyses and further constrains the use of such detectors in the pharmaceutical field: pharmacopoeias recommend detectors whose response is linear.

In order to overcome this disadvantage, document EP-1 275 961 has already proposed a method for controlling an evaporative light scattering detector which consists in adjusting at least one parameter which influences the nebulising conditions upstream of the evaporation chamber of the aerosol in order to fix the response coefficient of the detector at an adjustment value so as to facilitate the analyses and/or increase the precision and reliability thereof.

According to this prior document, the parameters influencing the nebulising conditions can be the nature of the nebulising gas, the temperature of this gas, the temperature of the nebulising chamber and/or the composition of the carrier liquid.

In particular, it has been proposed to add to the mobile phase, upstream of the evaporative light scattering detector, a modifying agent at a specific concentration so as to obtain solvation or complexing of the analytes in order to facilitate the analyses and/or to increase the precision and the reliability thereof.

Furthermore, the literature has already disclosed a number of cases of great variation in response coefficient b of an evaporative light scattering detector with the flow of the mobile phase, the nature of the nebulising gas or the nature of the mobile phase.

In this manner, it has been possible to obtain values for coefficient b which are approximately unity for low flow rates (M. Rajevic, P. J. Betto, J. Liq. Chrom. & Rel. Techn. 21(18), (1998), 2821), or for micro-flows with a micro-nebuliser (S. Héron, A. Tchapla, J. Chromatogr. A, 848, (1999) 95 and Ph. D, F. Guerrero, LYON I, No. 12-95, 25 Jan. 1995).

According to the publication Y. Mengerik, H. J. C. De Man, Sj. S. Van Der Wal, J. Chromatogr. 552, (1991) 593, intensity A of the signal is greater with helium than with nitrogen, air or carbon dioxide.

According to the publication, F. S. Deschamps, K. Gaudin, E. Lesellier, A. Tchapla, D. Ferrier, A. Baillet, P. Chaminade, Chromatographia, 54, (2001), 607, and that of C. Elfakir, P. Chaimbault, M. Dreux, J. Chromatogr. 829; (1998), 193, it is probable that some mobile phases allow modification of the nature of some analytes and, consequently, an increase in the intensity of signal A, and therefore the detection of these analytes to be made more sensitive.

According to these prior documents, however, the detection in the evaporative light scattering detector was necessarily dependent on the mobile phase used for the chromatographic separation both in terms of the nature and the flow thereof.

The method according to the invention allows this disadvantage to be overcome.

To this end, and according to a preferred feature of the invention, the nature and the flow of the carrier fluid are selected so as to fix response coefficient b of the evaporative light scattering detector at an adjustment value so as to facilitate the analyses, and/or to increase the precision and reliability thereof, slope b of the calibration curves being determined by the equation:

$$\text{Log } A = b \text{ Log } m + \text{Log } a$$

where A represents the area of the signal which measures the intensity emitted by one of the compounds to be analysed and m is the mass or the concentration of this compound in the sample.

According to the invention, the adjustment value can be either a value of approximately unity or a value which is as large as possible.

In the first case, that is to say, when slope b of the calibration curves is as close as possible to unity, or ideally equal to 1, the signal supplied by the evaporative light scattering detector is directly proportional to the mass or the concentration of the compounds to be analysed.

It will be appreciated that such direct linearity between the intensity of the signal supplied by the apparatus and the quantity of compounds responsible for this signal is able to broadly facilitate the analyses and increase the precision and reliability thereof in some cases.

Obtaining a slope b whose value is as large as possible is also particularly advantageous: for a given variation in the concentration of a compound to be analysed, the intensity of the signal supplied by the apparatus increases as slope b becomes steeper.

Consequently, the sensitivity of the analysis increases with the value of slope b of the calibration curves.

According to the invention, it is necessary to mix the successive fractions of the flow which originates from the chromatography column and the carrier fluid which conveys these fractions upstream of the evaporative light scattering detector.

Such a mixture is completely necessary in order to produce reproducible analyses and satisfactory control of the response of the detector.

However, this mixture must not involve an excessively large broadening of the transferred fractions in order not to limit the analysis of complex mixtures or increase the detection limit.

Consequently, the flow of the carrier fluid cannot be arbitrary, that is to say, it must be neither too large (several milliliters per minute) nor too small (a few micro liters per minute).

The need for such a mixture makes it necessary to provide, in the secondary circuit between the flow-division valve and the evaporative light scattering detector, a specific mixing device which can, by way of example, be constituted by a glass frit or a mixing chamber having a very small dead volume.

Owing to the use of an active flow-division valve, an auxiliary pump and a mixing device, the method according to the invention allows not only control of response coefficient b of an evaporative light scattering detector, but further offers the advantage of allowing the use of such a detector to be generalised by automatically converting volatile molecules into less volatile types, as suggested by D. L. Ford and W. Kennard J. Oil Colour Chem. Ass. 49, (1966), 607, in the first publication to describe this type of detection.

In this manner, and owing to a judicious choice of the carrier fluid supplied by the auxiliary pump, it is possible to carry out successively, in the secondary circuit, the conversion by solvation or complexing of volatile analytes into less volatile types.

According to another feature of the invention, an auxiliary chromatography column is connected to the secondary circuit upstream of the evaporative light scattering detector.

This feature allows a second separation, which is completely independent of the first separation, to be linked to the first separation when the various constituents of the mixture to be analysed have not been sufficiently separated on the first chromatography column.

A second separation of this type is made possible by the use of monolith stationary phases type which can work effectively, even at low pressure, which calls upon in particular the principle of transfers by means of the valve used in the assembly.

What is claimed is:

1. Method allowing control of an evaporative light scattering detector which is coupled to a liquid chromatography column, substantially independently of the elution conditions for the chromatographic separation, characterised in that a given adjustable constant calibrated volume of the flow which originates from the chromatography column is removed at a given adjustable frequency, this flow being constituted by an eluent which contains compounds to be analysed which have been dissolved therein, and the volume removed in this manner is transferred to a secondary circuit, to which the evaporative light scattering detector is connected, by being conveyed by means of an auxiliary pump with a specific carrier fluid which is independent of the eluent and which has a predetermined flow, and the successive fractions of the flow which originates from the chromatography column are mixed with the carrier fluid which conveys these fractions upstream of the evaporative light scattering detector.

2. Method according to claim 1, characterised in that it is used to control an evaporative light scattering detector which is coupled to a liquid chromatography column in the case of separation by elution gradient so as to attenuate the variations in the response of the evaporative light scattering detector in accordance with the nature of the eluent.

3. Method according to claim 1, characterised in that, in the presence of majority compounds and minority compounds, the calibrated volumes transferred to the secondary circuit and the transfer frequency are varied during analysis.

4. Method according to claim 1, characterised in that the nature and the flow of the carrier fluid are selected so as to fix response coefficient (b) of the evaporative light scattering detector at an adjustment value so as to facilitate the analyses and/or to increase the precision and reliability thereof, slope (b) of the calibration curves being determined by the equation:

$$\text{Log } A = b \text{ Log } m + \text{Log } a$$

where A represents the area of the signal which measures the intensity emitted by one of the compounds to be analysed and m is the mass or the concentration of this compound in the sample.

5. Method according to claim 1, characterised in that the adjustment value (b) is a value of approximately unity.

6. Method according to claim 1, characterised in that the adjustment value (b) is the maximum possible value.

7. Method according to claim 1, characterised in that an auxiliary chromatography column is connected to the secondary circuit upstream of the evaporative light scattering detector.

* * * * *